US006583277B2

(12) United States Patent
Luo et al.

(10) Patent No.: US 6,583,277 B2
(45) Date of Patent: Jun. 24, 2003

(54) SEMAPHORIN K1

(75) Inventors: Yuling Luo, South San Francisco, CA (US); Xiaomei Xu, South San Francisco, CA (US)

(73) Assignee: Exelixis, Inc., South San Francisco, CA (US)

( * ) Notice: Subject to any disclaimer, the term of this patent is extended or adjusted under 35 U.S.C. 154(b) by 164 days.

(21) Appl. No.: 09/771,467

(22) Filed: Jan. 26, 2001

(65) Prior Publication Data

US 2002/0177549 A1 Nov. 28, 2002

Related U.S. Application Data

(62) Division of application No. 09/041,236, filed on Mar. 11, 1998, now Pat. No. 6,225,285.

(51) Int. Cl.[7] ................................................ C07H 21/04
(52) U.S. Cl. ..................... 536/23.5; 536/23.1; 530/300; 530/327; 530/324; 530/350; 435/69.1
(58) Field of Search ............... 536/23.1, 23.5; 435/69.1, 70.1, 41, 466; 530/300, 324, 327, 350

(56) References Cited

U.S. PATENT DOCUMENTS 6,197,544 B1 * 3/2001 Michalovich et al.

OTHER PUBLICATIONS

Ensser et al. GenEmbl Accession No. AF 030690, submitted Oct. 21, 1997.
Sambrook et al. Molecular Cloning, CSH, 1989.

* cited by examiner

*Primary Examiner*—Lynette R. F. Smith
*Assistant Examiner*—Robert A. Zeman
(74) *Attorney, Agent, or Firm*—Richard Aron Osman

(57) ABSTRACT

The invention provides methods and compositions relating to semaphorin K1 (sema K1) polypeptides which regulate cellular guidance and physiology, and related nucleic acids. The polypeptides may be produced recombinantly from transformed host cells from the disclosed sema K1 encoding nucleic acids or purified from human cells. The invention provides isolated sema K1 hybridization probes and primers capable of specifically hybridizing with the disclosed sema K1 genes, sema K1-specific binding agents such as specific antibodies, and methods of making and using the subject compositions in diagnosis, therapy and in the biopharmaceutical industry.

16 Claims, No Drawings

SEMAPHORIN K1

This application is a divisional application of and claims priority under 35 U.S.C. §120 to U.S. Ser. No. (09/041,236, filed Mar. 11, 1998, now U.S. Pat. No. 6,225,285, which is incorporated herein by reference.

FIELD OF THE INVENTION

The field of this invention is polypeptides involved in cell guidance.

BACKGROUND

The semaphorins constitute a large family of evolutionally conserved glycoproteins that are defined by a characteristic semaphorin domain of approximately 500 amino acids (1–3). The first vertebrate semaphorin, collapsin-1 in chick, was identified by its ability to induce growth cone collapse (4). Consistent with this function, its mammalian homologue, sema III, has been shown to repel specific subsets of sensory axons (5). As a result of these and other studies, Coll-1/sema III/D has been implicated in the patterning of sensory axon projections into the ventral spinal cord and cranial nerve projections into the periphery (6–11).

Several other semaphorins have also been implicated as repulsive and/or attractive cues in axon guidance, axon fasciculation, and synapse formation (1, 12–17). In addition, members of semaphorin family have been implicated in functions outside the nervous system, including bone skeleton and heart formation (9), immune function (18, 19), tumor suppression (20–22), and conferring drug resistance to cells (23).

Recent studies have identified the first semaphorin receptor as a member of the neuropilin family. Neuropilin-1 is a high affinity receptor for sema III, E and IV, whereas neuropilin-2 binds differentially to the subfamily of secreted semaphorins (24–27).

The vertebrate semaphorin family can be classified into several phylogenetically distinct subfamilies (15). Each subfamily has a unique structural arrangement of protein domains. The secreted members of the semaphorin family contain a characteristic semaphorin domain at the N-terminus, followed by an immunoglobulin (Ig) domain and a stretch of basic amino acids in the carboxyl-terminal region. Between the N-terminal semaphorin domain and the transmembrane spanning region, the transmembrane semaphorins contain several alternative structural motifs including either an Ig domain, a stretch of thrombospondin repeats, or a sequence with no obvious domain homology. Interestingly, semaphorin-like sequences have been identified in the genomes of poxviruses (1) and alcelaphine herpesvirus-1 (28), occupying unique branches of the semaphorin phylogenetic tree. Here we report the identification of a GPI-linked human semaphorin—semaphorin K1—which is homologous to the semaphorin encoded by alcelaphine herpesvirus-1 and show that semaphrin K1 polypeptides and nucleic acids are bioactive in modulating nervous and immune system function.

CITED LITERATURE

Cited Literature

1. Kolodkin, A.-L., Matthes, D.-J. & Goodman, C.-S. (1993) Cell, 75, 1389–1399
2. Puschel, A.-W., Adams, R.-H. & Betz, H. (1995) Neuron, 14, 941–948.

-continued

Cited Literature

3. Luo, Y., et al. (1995) Neuron 14, 1131–1140.
4. Luo, Y., Raible, D. & Raper, J.-A. (1993) Cell, 75, 217–227.
5. Messersmith, E.-K., et al. (1995) Neuron 14, 949–959.
6. Fan, J. & Raper, J.-A. (1995) Neuron, 14, 263–274.
7. Kobayashi, H., et al. (1997) J. Neurosci. 17, 8339–8352.
8. Puschel, A.-W., Adams, R.-H. & Betz, H. (1996) Mol. Cell. Neurosci. 7, 419–431.
9. Behar, O., et al. (1996) Nature, 383, 525–528.
10. Shepherd, I.-T., et al. (1997) Development, 124, 1377–1385.
11. Taniguchi, M., et al. (1997) Neuron 19, 519–530.
12. Kolodkin, A. L., et al. (1992). Neuron 9, 831–845.
13. Matthes, D.-J., et al. (1995) Cell 81, 631–639.
14. Wong, J. T., Yu, W. T., O'Connor, T. P. (1997) Development 124, 3597–3607.
15. Adams, R.-H., Betz, H., & Puschel, A.-W. (1996) Mech Dev. 57, 33–45.
16. Feiner, L., et al. (1997) Neuron 19, 539–545.
17. Yu, H-H., Araj, H.-H., Ralls, S.-A. & Kolodkin A.-L. (1998) Neuron 20, 207–220.
18. Bougeret, C., et al. (1992) J. Immunol. 148, 318–323.
19. Hall, K.-T., et al. (1995) Proc. Natl. Acad. Sci. 93, 11780–11785.
20. Xiang, R.-H., et al al. (1996) Genomics, 32, 39–48.
21. Roche, J., et al. (1996) Oncogene 12, 1289–1297.
22. Sekido, Y., et al. (1996) Proc. Natl. Acad. Sci. 93, 4120–4125.
23. Yamada, T., et al. (1997) Proc. Natl. Acad. Sci. 94, 14713–14718.
24. He, Z. & Tessier-Lavigne, M. (1997) Cell 90, 739–751.
25. Kolodkin, A.-L., et al. (1997) Cell, 90, 753–762.
26. Chen, H., et al. (1997) Neuron 19, 547–559.
27. Kitsukawa, T., et al. (1997) Neuron 19, 995–1005.
28. Ensser. A. & Fleckenstein, B. (1995) J. Gen. Virol. 76, 1063–1067.
29. Frohman, M. A. (1993) Methods Enzymol. 218, 340–356.
30. Koppel, A.-M., et al. (1997) Neuron 19, 531–537.
31. Eickholt, B. J., et al. (1997) Mol. Cell Neurosci, 9, 358–371.
32. Schaeren-Wiemers, N. & Gerfin-Moser, A. (1993) Histochemistry 100, 431–440.
33. Altschul, S.-F., et al. (1990) J. Mol. Biol. 215, 403–410.
34. Kyte, J & Doolittle, R. F. (1982) J. Mol. Biol. 157, 105–132.
35. von Heijne, G. (1985) J. Mol. Biol. 184, 99–105.
36. Udenfriend, S. & Kodukula, K. (1995) Annu. Rev. Biochem. 64, 563–591.
37. Higgins, D. J., et al. (1996) Methods Enzymol. 266, 383–402.

SUMMARY OF THE INVENTION

The invention provides methods and compositions relating to semaphorin K1 (sema K1) polypeptides, related nucleic acids, polypeptide domains thereof having sema K1-specific structure and activity and modulators of sema K1 function. The polypeptides may be produced recombinantly from transformed host cells from the subject sema K1 polypeptide encoding nucleic acids or purified from mammalian cells. The invention provides isolated sema K1 gene hybridization probes and primers capable of specifically hybridizing with the disclosed sema K1-encoding genes, sema K1-specific binding agents such as specific antibodies, and methods of making and using the subject compositions in diagnosis (e.g. nucleic acid hybridization screens for sema K1 transcripts), modulating cellular physiology (e.g. by contacting with exogenous sema K1) and in the biopharmaceutical industry (e.g. as immunogens, reagents for isolating other semaphorins, reagents for screening chemical libraries for lead pharmacological agents, etc.).

DETAILED DESCRIPTION OF THE INVENTION

The nucleotide sequence of a natural cDNA encoding a human sema K1 polypeptide is shown as SEQ ID NO:1, and the full conceptual translate is shown as SEQ ID NO:2. The sema K1 polypeptides of the invention include one or more functional domains of SEQ ID NO:2, which domains comprise at least one of (a) SEQ ID NO:2, (b) at least 100 contiguous residues of SEQ ID NO:2, (c) at least 60 contiguous residues of SEQ ID NO:2, residues 340–634, and (d) at least 12 contiguous residues of SEQ ID NO:2, residues 481–634. A cDNA encoding an alcelaphine herpesvirus semaphorin having sequence similarity to the subject sema K1 polypeptides, and its translate are shown as SEQ ID NO:3 and 4, respectively. Sema K1 specific polynucleotides and polypeptides having human sema K1-specific sequences are readily discernable from alignments of the sequences. Preferred sema K1 polypeptides have one or more human sema K1-specific activities, such as cell surface receptor binding and/or binding inhibitory activity and sema K1-specific immunogenicity and/or antigenicity.

Sema K1-specific activity or function may be determined by convenient in vitro, cell-based, or in vivo assays: e.g. in vitro binding assays, cell culture assays, in animals (e.g. gene therapy, transgenics, etc.), etc. Binding assays encompass any assay where the molecular interaction of an sema K1 polypeptide with a binding, target is evaluated. The binding target may be a natural extracellular binding target such as a nerve or immune cell surface protein; or non-natural binding target such a specific immune protein such as an antibody, or an sema K1 specific agent such as those identified in screening assays such as described below. Sema K1-binding specificity may be assayed by binding equilibrium constants (usually at least about $10^7$ $M^{-1}$, preferably at least about $10^8$ $M^{-1}$, more preferably at least about $10^9$ $M^{-1}$), by growth cone collapse assays, by the ability to elicit sema K1 specific antibody in a heterologous host (e.g. a rodent or rabbit), etc.

For example, deletion mutagenesis is used to define functional sema K1 domains which specifically bind nerve or immune cell surface proteins in cell-based assays described below.

TABLE 1

Exemplary sema K1 deletion mutants defining sema K1 functional domains.

| Mutant | Sequence | Nerve Cell Binding | Immune Cell Binding |
|---|---|---|---|
| ΔN1 | SEQ ID NO: 2, residues 8–606 | + | + |
| ΔN2 | SEQ ID NO: 2, residues 18–606 | + | + |
| ΔN3 | SEQ ID NO: 2, residues 26–606 | + | + |
| ΔN4 | SEQ ID NO: 2, residues 39–606 | + | + |
| ΔN5 | SEQ ID NO: 2, residues 48–606 | + | + |
| ΔC1 | SEQ ID NO: 2, residues 1–601 | + | + |
| ΔC2 | SEQ ID NO: 2, residues 1–592 | + | + |
| ΔC3 | SEQ ID NO: 2, residues 1–584 | + | + |
| ΔC4 | SEQ ID NO: 2, residues 1–573 | + | + |
| ΔC5 | SEQ ID NO: 2, residues 1–566 | + | + |
| ΔNC1 | SEQ ID NO: 2, residues 24–587 | + | + |
| ΔNC2 | SEQ ID NO: 2, residues 12–568 | + | + |
| ΔNC3 | SEQ ID NO: 2, residues 41–601 | + | + |
| ΔNC4 | SEQ ID NO: 2, residues 6–561 | + | + |
| ΔNC5 | SEQ ID NO: 2, residues 55–605 | + | + |

In a particular embodiment, the subject domains provide sema K1-specific antigens and/or immunogens, especially when coupled to carrier proteins. For example, peptides corresponding to sema K1-and human sema K1-specific domains are covalently coupled to keyhole limpet antigen (KLH) and the conjugate is emulsified in Freunds complete adjuvant. Laboratory rabbits are immunized according to conventional protocol and bled. The presence of sema K1-specific antibodies is assayed by solid phase immunosorbant assays using immobilized sema K1 polypeptides of SEQ ID NOS2, see, e.g. Table 2.

TABLE 2

Immunogenic sema K1 polypeptides eliciting sema K1-specific rabbit polyclonal antibody: sema K1 polypeptide-KLH conjugates immunized per protocol described above.

| Sema K1 Polypeptide Sequence | Immunogenicity |
|---|---|
| SEQ ID NO: 2, residues 1–10 | +++ |
| SEQ ID NO: 2, residues 12–21 | +++ |
| SEQ ID NO: 2, residues 25–37 | +++ |
| SEQ ID NO: 2, residues 42–59 | +++ |
| SEQ ID NO: 2, residues 62–71 | +++ |
| SEQ ID NO: 2, residues 72–85 | +++ |
| SEQ ID NO: 2, residues 88–89 | +++ |
| SEQ ID NO: 2, residues 105–112 | +++ |
| SEQ ID NO: 2, residues 116–122 | +++ |
| SEQ ID NO: 2, residues 120–128 | +++ |
| SEQ ID NO: 2, residues 175–182 | +++ |
| SEQ ID NO: 2, residues 180–195 | +++ |
| SEQ ID NO: 2, residues 201–208 | +++ |
| SEQ ID NO: 2, residues 213–222 | +++ |
| SEQ ID NO: 2, residues 222–230 | +++ |
| SEQ ID NO: 2, residues 228–237 | +++ |
| SEQ ID NO: 2, residues 230–338 | +++ |
| SEQ ID NO: 2, residues 237–245 | +++ |
| SEQ ID NO: 2, residues 247–256 | +++ |
| SEQ ID NO: 2, residues 282–291 | +++ |
| SEQ ID NO: 2, residues 335–353 | +++ |
| SEQ ID NO: 2, residues 335–353 | +++ |
| SEQ ID NO: 2, residues 355–364 | +++ |
| SEQ ID NO: 2, residues 365–374 | +++ |
| SEQ ID NO: 2, residues 412–420 | +++ |
| SEQ ID NO: 2, residues 440–447 | +++ |
| SEQ ID NO: 2, residues 475–482 | +++ |
| SEQ ID NO: 2, residues 480–495 | +++ |
| SEQ ID NO: 2, residues 531–538 | +++ |
| SEQ ID NO: 2, residues 554–562 | +++ |
| SEQ ID NO: 2, residues 572–583 | +++ |
| SEQ ID NO: 2, residues 598–606 | +++ |

The claimed sema K1 polypeptides are isolated or pure: an "isolated" polypeptide is unaccompanied by at least some of the material with which it is associated in its natural state, preferably constituting at least about 0.5%, and more preferably at least about 5% by weight of the total polypeptide in a given sample and a pure polypeptide constitutes at least about 90%, and preferably at least about 99% by weight of the total polypeptide in a given sample. The sema K1 polypeptides and polypeptide domains ma! be synthesized, produced by recombinant technology, or purified from mammalian, preferably human cells. A wide variety of molecular and biochemical methods are available for biochemical synthesis, molecular expression and purification of the subject compositions, see e.g. Molecular Cloning, A Laboratory Manual (Sambrook, et al. Cold Spring Harbor Laboratory), Current Protocols in Molecular Biology (Eds. Ausubel, et al., Greene Publ. Assoc., Wiley-Interscience, NY) or that are otherwise known in the art.

The invention provides binding agents specific to sema K1 polypeptides, preferably the claimed sema K1 polypeptides, including agonists, antagonists, natural cell surface receptor binding targets, etc., methods of identifying and making such agents, and their use in diagnosis, therapy and pharmaceutical development. For example, specific binding agents are useful in a variety of diagnostic and therapeutic applications, especially where disease or disease prognosis is associated with improper utilization of a pathway involving the subject proteins. Novel sema K1-specific binding agents include sema K1-specific receptors, such as somatically recombined polypeptide receptors like specific antibodies or T-cell antigen receptors (see, e.g. Harlow and Lane (1988) Antibodies, A Laboratory Manual, Cold Spring Harbor Laboratory) and other natural binding agents such as Sema K1 cell surface receptors, non-natural intracellular binding agents identified in screens of chemical libraries such as described below etc. Agents of particular interest modulate sema K1 function, e.g. sema K1-modulatable cellular physiology, e.g. guidance.

Accordingly, the invention provides methods for modulating cell function comprising the step of modulating sema K1 activity, e.g. by contacting the cell with a sema K1 polypeptide, a sema K1 inhibitor, e.g. inhibitory sema K1 deletion mutants, sema K1-specific antibodies, etc. (supra). The target cell may reside in culture or in situ, i.e. within the natural host. The modulator may be provided in any convenient way, including by (i) intracellular expression from a recombinant nucleic acid or (ii) exogenous contacting of the cell. For many in situ applications, the compositions are added to a retained physiological fluid such as blood or synovial fluid. For CNS administration, a variety of techniques are available for promoting transfer of the therapeutic across the blood brain barrier including disruption by surgery or injection, drugs which transiently open adhesion contact between CNS vasculature endothelial cells, and compounds which facilitate translocation through such cells. Sema K1 polypeptides or polypeptide modulators may also be amenable to direct injection or infusion, topical, intratracheal/nasal administration e.g. through aerosol, intraocularly, or within/on implants e.g. fibers e.g. collagen, osmotic pumps, grafts comprising appropriately transformed cells, etc. A particular method of administration involves coating, embedding or derivatizing fibers, such as collagen fibers, protein polymers, etc. with therapeutic proteins. Other useful approaches are described in Otto et al. (1989) J Neuroscience Research 22, 83–91 and Otto and Unsicker (1990) J Neuroscience 10, 1912–1921. Generally, the amount administered will be empirically determined, typically in the range of about 10 to 1000 µg/kg of the recipient and the concentration will generally be in the range of about 50 to 500 µg/ml in the dose administered. Other additives may be included, such as stabilizers, bactericides, etc. will be present in conventional amounts. For diagnostic uses, the modulators or other sema K1 binding agents are frequently labeled, such as with fluorescent, radioactive, chemiluminescent, or other easily detectable molecules, either conjugated directly to the binding agent or conjugated to a probe specific for the binding agent.

The amino acid sequences of the disclosed sema K1 polypeptides are used to back-translate sema K1 polypeptide-encoding nucleic acids optimized for selected expression systems (Holler et al. (1993) Gene 136, 323–328; Martin et al. (1995) Gene 154, 150–166) or used to generate degenerate oligonucleotide primers and probes for use in the isolation of natural sema K1-encoding nucleic acid sequences ("GCG" software, Genetics Computer Group, Inc, Madison Wis). Sema K1-encoding nucleic acids used in sema K1-expression vectors and incorporated into recombinant host cells, e. for expression and screening, transgenic animals, e.g. for functional studies such as the efficacy of candidate drugs for disease associated with sema K1-modulated cell function, etc.

The invention also provides nucleic acid hybridization probes and replication/amplification primers having a sema K1 cDNA specific sequence comprising a strand of least one of: (a) SEQ ID NO:1, (b) at least 300 contiguous nucleotides of SEQ ID NO:1, (c) at least 102 contiguous nucleotides of SEQ ID NO:1, nucleotides 1017–2498, and (d) at least 36 contiguous nucleotides of SEQ ID NO:1, nucleotides 1441–2498, and sufficient to specifically hybridize with a second nucleic acid comprising the complementary strand of SEQ ID NO:1. Demonstrating specific hybridization generally requires stringent conditions, for example, hybridizing in a buffer comprising 30% formamide in 5×SSPE (0.18 M NaCl, 0.01 M NaPO$_4$, pH7.7, 0.001 M EDTA) buffer at a temperature of 42° C. and remaining bound when subject to washing at 42° C. with 0.2×SSPE; preferably hybridizing in a buffer comprising 50% formamide in 5×SSPE buffer at a temperature of 42° C. and remaining bound when subject to washing at 42° C. with 0.2×SSPE buffer at 42° C.

TABLE 3

Exemplary sema K1 nucleic acids which hybridize with a strand of SEQ ID NO: 1 under Conditions I and/or II.

| sema K1 Nucleic Acids | Hybridization |
|---|---|
| SEQ ID NO: 1, nucleotides 1–36 | + |
| SEQ ID NO: 1, nucleotides 68–98 | + |
| SEQ ID NO: 1, nucleotides 95–130 | + |
| SEQ ID NO: 1, nucleotides 175–220 | + |
| SEQ ID NO: 1, nucleotides 261–299 | + |
| SEQ ID NO: 1, nucleotides 274–310 | + |
| SEQ ID NO: 1, nucleotides 331–369 | + |
| SEQ ID NO: 1, nucleotides 430–470 | + |
| SEQ ID NO: 1, nucleotides 584–616 | + |
| SEQ ID NO: 1, nucleotides 661–708 | + |
| SEQ ID NO: 1, nucleotides 789–825 | + |
| SEQ ID NO: 1, nucleotides 928–965 | + |
| SEQ ID NO: 1, nucleotides 1017–1043 | + |
| SEQ ID NO: 1, nucleotides 1053–1072 | + |
| SEQ ID NO: 1, nucleotides 1073–1095 | + |
| SEQ ID NO: 1, nucleotides 1096–1113 | + |
| SEQ ID NO: 1, nucleotides 1132–1152 | + |
| SEQ ID NO: 1, nucleotides 1238–1255 | + |
| SEQ ID NO: 1, nucleotides 1275–1295 | + |
| SEQ ID NO: 1, nucleotides 1380–1400 | + |
| SEQ ID NO: 1, nucleotides 1430–1450 | + |
| SEQ ID NO: 1, nucleotides 1476–1498 | + |
| SEQ ID NO: 1, nucleotides 1545–1577 | + |
| SEQ ID NO: 1, nucleotides 1631–1654 | + |
| SEQ ID NO: 1, nucleotides 1765–1790 | + |
| SEQ ID NO: 1, nucleotides 1812–1833 | + |
| SEQ ID NO: 1, nucleotides 1944–1959 | + |
| SEQ ID NO: 1, nucleotides 2003–2021 | + |
| SEQ ID NO: 1, nucleotides 2121–2143 | + |
| SEQ ID NO: 1, nucleotides 2232–2250 | + |
| SEQ ID NO: 1, nucleotides 2378–2397 | + |
| SEQ ID NO: 1, nucleotides 2480–2498 | + |

The subject nucleic acids are of synthetic/non-natural sequences and/or are isolated, i.e. unaccompanied by at least some of the material with which it is associated in its natural state, preferably constituting at least about 0.5%, preferably at least about 5% by weight of total nucleic acid present in a given fraction, and usually recombinant, meaning they comprise a non-natural sequence or a natural sequence joined to nucleotide(s) other than that which it is joined to on a natural chromosome. Recombinant nucleic acids comprising the nucleotide sequence of SEQ ID NO:1, or requisite fragments thereof, contain such sequence or fragment at a terminus, immediately flanked by (i.e. contiguous with) a sequence other than that which it is joined to on a natural chromosome, or flanked by a native flanking region fewer than 10 kb, preferably fewer than 2 kb, which is at a terminus or is immediately flanked by a sequence other than that which it is joined to on a natural chromosome. While the nucleic acids are usually RNA or DNA, it is often advantageous to use nucleic acids comprising other bases or nucleotide analogs to provide modified stability, etc.

The subject nucleic acids find a wide variety of applications including use as translatable transcripts, hybridization probes, PCR primers, diagnostic nucleic acids, etc.; use in detecting the presence of sema K1 genes and gene transcripts and in detecting or amplifying nucleic acids encoding additional sema K1 homologs and structural analogs. In diagnosis, sema K1 hybridization probes find use in identifying wild-type and mutant sema K1 alleles in clinical and laboratory samples. Mutant alleles are used to generate allele-specific oligonucleotide (ASO) probes for high-throughput clinical diagnoses. In therapy, therapeutic sema K1 nucleic acids are used to modulate cellular expression, concentration or availability of active sema K1.

The invention provides efficient methods of identifying agents, compounds or lead compounds for agents active at the level of a sema K1 modulatable cellular function. Generally, these screening methods involve assaying for compounds which modulate sema K1 interaction with a natural sema K1 binding target. A wide variety of assays for binding agents are provided including labeled in vitro protein-protein binding assays, immunoassays, cell based assays, etc. The methods are amenable to automated, cost-effective high throughput screening of chemical libraries for lead compounds. Identified reagents find use in the pharmaceutical industries for animal and human trials; for example, the reagents may be derivatized and rescreened in vitro and in vivo assays to optimize activity and minimize toxicity for pharmaceutical development.

The following experimental sections/examples are offered by way of illustration and not by way of limitation.

EXAMPLES

Cloning of Sema K1. Four human ESTs, R33537, W47265, R33439, H03806, and one mouse EST, AA260340, were identified that show highest homology with the semaphorin gene in alcelaphine herpesvirus-1 (AHV sema). Oligos corresponding to the sequences of human ESTs were used to amplify by PCR a cDNA fragment from a human testis cDNA library (GIBCO BRL). This PCR fragment corresponds to the central portion of sema K1. The 3' end was cloned by rapid amplification of cDNA ends (RACE) using human placenta Marathon-Ready cDNA from Clontech (29). The remaining 5' end was cloned by PCR amplification from a Clontech human brain λgt11 cDNA library using an internal primer from sema K1 and an anchor primer corresponding to the λgt11 vector sequence. A specific PCR product corresponding to the 5' end was identified by Southern Blot using sema K1 oligos as probes. The full length cDNA of human sema K1 except the region corresponding to the signal peptide sequence was independently cloned from Clontech human placenta λgt10 library by high fidelity PCR amplification and its DNA sequence reconfirmed.

Expression Constructs. Three expression constructs were made that allow the expression of recombinant proteins tagged with either a myc-his tag at the carboxyl terminus (pEX-mh), an alkaline phosphatase tag at the amino terminus and a myc-his tag at the carboxyl terminus (pEX-AP), or an Fc domain of human immunoglobulin at the carboxyl terminus (pEX-Fc). Similar expression constructs have been made for collapsins and semaphorins and the resulting fusion proteins were shown to be filly functional (7, 10, 23, 24, 30, 31). The multiple cloning site of pSecTagA (Invitrogen) was excised with Pme I and Nhe I and cloned into pcDNA3.1 (Invitrogen) to make myc-his tagged vector pEX-mh. This expression vector contains a signal peptide sequence from immunoglobulin kappa chain for protein secretion. The cDNA for human placental alkaline phosphatase was PCR amplified from pSEAP (Clontech) and cloned into the SfiI site of pEX-mh maintaining the original reading frame to make the AP-tagged vector pEX-AP. The Fc domain of human IgG1 and an enterokinase cleavage site were PCR amplified from Signal-pIgplus (Novagen) and cloned into the Apa I to Pme I sites of pEX-mh maintaining the original reading frame to make the Fc-tagged vector pEX-Fc. Various cDNAs for full length sema K1, extracellular domain of sema K1 (residues starting from Gly-612 to the carboxyl terminal end were deleted), sema III, and neuropilin-1 were PCR amplified from cDNA libraries and subcloned into these expression vectors. The neuropilin-2 expression construct was as previously described (25).

Cell Surface Staining. COS-7 cells were transiently transfected with the full length sema K1 in pEX-AP vector using lipofectamine (GIBCO-BRL). Two days after transfection, cells were washed and treated with or without PI-PLC (Boehringer Mannheim) at 250 mU/ml for 1 hour at 37° C. Cells were then fixed in 4% paraformaldehyde for 10 min at room temperature. After PBS wash, cells were incubated with a rabbit anti-AP antibody (Accurate Antibodies) at a dilution of 1:500 for one hour followed by a Cy3-anti-rabbit antibody at a dilution of 1:200. The fluorescent images of the transfected cells were photographed in a Zeiss microscope using a 40× lens.

Western Blotting. COS-7 cells were transiently transfected with the full length sema K1 in pEX-AP vector with Lipofectamine (GIBCO-BRL). Cells transfected with the full length CD100 in pEX-AP served as a control. Two days after transfection, cells were incubated with or without 250 mU/ml of PI-PLC (Boehringer Mannheim) for 1 hour at 37° C. Supernatants and cell lysates were collected and run on a 4–20% SDS-PAGE gel and the AP-tagged sema K1 protein was detected with a BRP-conjugated anti-alkaline phosphatase antibody.

Protein Expression. Stable 293 cell lines secreting myc-his tagged, AP-tagged, or Fc-tagged sema K1 and sema III were derived from transfection of various expression plasmids followed by G418 selection. Conditioned media from stably transfected cell lines were collected and were confirmed for the expression and integrity of recombinant proteins by Western Blot using anti-AP, anti-Fc, or anti-myc antibodies. SDS-PAGE gel demonstrated that sema K1-Fc fusion protein migrates as a dimer linked by the disulfide bonds in the Fc region, while the sema K1-mh and AP-sema K1 are monomeric. Approximately equal amount of AP- or Fc-tagged sema III and sema K1 fusion proteins as judged by Western Blot were used in the ligand binding experiments. The amount of active sema III used for the ligand binding experiment was further quantified by a growth cone collapse assay and estimated to be over 80 collapsing units/ml (4, 7).

Ligand Binding Experiments. COS-7 cells were transiently transfected with fill length neuropilin-1 or neuropilin-2 expression constructs with FuGENETM 6 (Boehringer Mannheim). The expression of neuropilin-1 or -2 was confirmed using a monoclonal antibody 9E10 against the myc tag at the carboxyl terminal ends of both receptors. After two days of transfection, the cells were then incubated with supernatants containing approximately equal amount of sema III-Fc or sema K1-Fc for 1 hour. After post-fixing in 1% paraformaldehyde for 10 min, the cells were heat-inactivated at 65° C. for 1 hour to destroy the endogenous alkaline phosphatase activity. Cells were then incubated with alkaline phosphatase-conjugated anti-Fc antibody at 1:500 dilution for 1 hour and processed for chromogenic AP enzymatic reaction.

For the immune cell staining experiment, P388D1 or RBL-2H3 cells were fixed in 1% paraformaldehyde for 10 min. The suspension cells (A20 and Jurkat) were washed in PBS once and fixed in 1% paraformaldehyde for 10 min and then cytospun onto glass slides. After blocking for 30 min, AP-sema K1 or AP-sema III containing supernatants were added to each well and incubated for 1 hour. The cells were then post-fixed in 100% methanol for 10 min, and the endogenous AP activity was heat-inactivated at 65° C. for 1 hour. Cells were then processed for chromogenic AP enzymatic reactions. AP alone was used as a negative control. For experiments in which sema K1-mh or sema III-mh were used to compete with AP-sema K1 or AP-sema III binding, respectively, sema K1-mh or sema III-mh was incubated with different cell lines for 30 minutes at room temperature prior to AP-sema K1 or AP-sema III incubation.

In Situ Hybridization. A 298 bp DNA fragment corresponding to the sequence of mouse EST AA260340 was PCR amplified from a mouse cDNA library. This DNA fragment is predicted to encode a mouse homologue of human sema K1 based on the fact that it shares over 95% amino acid identity with the corresponding region of human sema K1. It was used as a probe in the in situ hybridization experiments. In situ hybridization procedure was performed on cryostat sections of E11, E15 mouse embryos and on brain and spinal cord sections of P3 and 5 week old mice as described (32). Tissues were fixed in 4% paraformaldehyde for four hours at 4° C. and embedded in OTC embedding compound. 20 ?m sections were cut and were treated with 1.0 µg/ml proteinase K for 15 min at 37° C., 0.2 MHCl for 20 min, and then acetylated for 10 min with 0.1M triethanolamine and 0.25% acetic anhydride. Sections were prehybridized for one hour at 65° C., then hybridized with digoxigenin-labeled probes (2 µg/ml) overnight at 55° C. The hybridization buffer consists of 50% formamide, 5×SSC, 10% dextran sulfate, 1×Denhardt's, 0.25 mg/ml tRNA, 0.1 mg/ml ssDNA. After hybridization, slides were washed with 0.2×SSC for 60 min at 65° C. and detected with an AP-conjugated anti-digoxigenin antibody at a dilution of 1:2000.

Semaphorin K1 is highly homologous to a viral semaphorin. In an effort to identify veterbrate homologues of viral semaphorins, we have searched existing EST databases against semaphorin-like sequences found in vaccinia virus and in alcelaphine herpesvirus-1 using the BLAST algorithm (33). Four human and one mouse ESTs were identified, which encode novel sequences that were most homologous to the semaphorin gene in alcelaphine herpesvirus-1 (AHV sema, 28). PCR primers were designed based on the EST sequences and were used to obtain a 2.5 kb cDNA that encodes a candidate semaphorin gene. The cDNA contains all the human EST sequences and encodes a protein of 634 amino acids with a molecular mass of 71.5 kDa. This protein is named semaphorin K1 (sema K1). Hydropathy analysis of the sema K1 sequence (34) indicates that the sema K1 sequence lacks approximately half of the signal peptide sequence required for protein secretion (35) Consistently, the alignment between AHV sema and sema K1 also showed an eight amino acid difference at the amino terminal end of sema K1. The hydropathy analysis also identified a long stretch of hydrophobic residues at the carboxyl-terminal end, a signal peptide sequence required for GPI-anchorage (36). This sema K1 protein represents a paradignmatic GPI-linked membrane protein in the semaphorin family.

The sequence of sema K1 is closely related to that of AHV sema. While 50% of amino acid identities are shared between the sema domains of sema K1 and AH, sema, less than 30% of amino acid identities are shared between the sema domains of sema K1 and other known semaphorins. In addition, 17 out of 18 cysteine residues and 4 out of 5 potential N-linked glycosylation sites are conserved. The homology extends throughout the entire amino acid sequences of sema K1 and AHV sema except at the carboxyl-terminal end, where only sema K1 contains the signal peptide sequence for GPI-anchorage. Thus, sema K1 appear to be a GPI-anchored membrane protein while AHV sema is a secreted protein. The unique structural arrangement of sema K1 defines a new subfamily of vertebrate semaphorins. Consistently, protein sequence homology analysis showed that sema K1 and AHV sema belong to the same branch of the dendrogram tree and this branch is distinct from that of other semaphorins Sequence alignment with other semaphorins also revealed that members of the viral-related semaphorin subfamily lack three tryptophan residues conserved in other semaphorins, indicating a structurally distinct viral sema domain.

Semaphorin K1 is a GPI-anchored membrane protein. To confirm that sema K1 is a GPI-anchored membrane protein, we have transfected COS-7 cells with a sema K1 expression construct and determined the localization of the expressed sema K1 protein. In order to track sema K1 protein expression, an AP-tagged version of sema K1 was engineered in which the human placenta alkaline phosphatase was fused to the fill length sema K1 at the N-terminus. This fusion protein can be detected with an anti-AP antibody. Upon transfection of the expression construct into COS-7 cells, the sema K1 fusion protein was detected on the surface of those transfected cells. Treatment with phosphatidylinositol-specific phospholipase C (PI-PLC) resulted in a complete removal of the fusion protein from cell surfaces. To examine whether the release of sema K1 fusion protein from cell surfaces is a specific action of PI-PLC rather than the result of random proteolysis, we compared the presence of this fusion protein in the supernatant and lysate of transfected COS-7 cells with or without PI-PLC treatment. Supernatants and lysates from PI-PLC treated or untreated cells were subjected to Western Blot analysis A 150 kDa protein corresponding to the predicted size of the fusion protein was detected with the anti-AP antibody. When the transfected COS-7 cells were not treated with PI-PLC, most, if not all, of the fusion protein was found to be associated with the cell lysate. Treatment of these cells with PI-PLC resulted in significant release of the fusion protein from the cell lysate into the supernatant, without apparent proteolysis. In a control experiment. PI-PLC treatment did not release the transmembrane semaphorin CD 100 into the cell supernatant. Furthermore, when a stop codon was introduced immediately N-terminal to the predicted signal peptide sequence for GPI-linkage, the resultant sema K1 protein was released to the cell supernatant (see below). Thus, we conclude that sema K1 is attached to the cell membrane via a GPI linkage.

Semaphorin K1 binds to specific immune cell lines. Neuropilin-1 and neuropilin-2 have recently been identified as receptors or components of a receptor complexes for sema III and other secreted semaphorins (24–26). To determine whether sema K1 could use neuropilin-1 or -2 as its receptor, we tested the ability of sema K1 to bind COS-7 cells transfected with neuropilin expression constructs. Soluble sema K1 fusion proteins containing either an AP tag at the N-terminus (AP-sema K1), an Fc domain of human IgG1 at the C-terminus (sema K1-Fc), or a myc-his tag at the C-terminus (sema K1-mh) were produced and were used in the ligand binding assay. Similarly arranged AP-sema III, sema III-Fc, and sema III-mh fusion proteins were prepared as controls. To test for interactions with neuropilin-1 or -2, sema K1-Fc or AP-sema K1 were incubated with neuropilin-expressing COS-7 cells, and ligand binding was detected using an anti-Fc antibody or a chromogenic AP enzymatic reaction. Under conditions where sema III-Fc binds to COS-7 cells expressing neuropilin-1 or -2, the dimerized sema K1-Fc does not bind to either (note that sema III binds to neuropilin-2 with lower affinity than to neuropilin-1). Similarly, under conditions when AP-sema III can bind to COS-7 cells expressing neuropilin-1 or -2, the monomeric AP-sema K1 does not bind to these cells. Thus, sema K1 does not bind neuropilin-1 or -2 with high affinity, and may not act through these receptors.

To determine whether or not the soluble sema K1 fusion proteins are competent to bind a cognate receptor and to provide an entry point for investigating the role of sema K1 in modulating immune function, we analyzed several immune cell lines for the presence of sema K1 binding sites. AP-sema K1 or AP-sema III were incubated with Jurkat T cells, A20 B cells, P388D1 macrophazes, and RBL-2H3 mast cell lines and the bound ligands were detected with chromogenic AP enzymatic reaction. AP-sema K1 bounds only to the cell surfaces of P388D1 macrophage and RBL-2H3 mast cell lines. This binding is specific, since AP alone does not bind to any of the cell lines and the binding could be competed by preincubation with sema K1-mh. In comparison, AP-sema III binding was detected on cell surfaces of all four immune cell lines tested. This binding is also specific, since preincubation of these cells with sema III-mh blocks the binding. The ability of sema III-Fc or sema K1-Fc to bind these four cell lines was also tested and similar results obtained. We conclude that sema III can bind the four immune cell lines tested, which contrasts with the more selective binding of sema K1 to macrophage and mast cell lines, suggesting the existence of a specific receptor for sema K1 in these cell lines.

Semaphorin K1 is preferentially expressed in postnatal and adult brain and spinal cord. In order to help define the biological role of sema K1, we examined the expression of sema K1 by Northern blot analysis and in situ hybridization. A 298 bp cDNA corresponding to the mouse homologue of human sema K1 was used as a probe in these studies. This probe does not cross-hybridize with the mRNA of other semaphorins. Northern blot analysis of mRNA isolated from adult mouse tissues revealed a single sema K1 transcript at 4.4 kb. The sema K1 transcript is highly expressed in brain, spinal cord, lung, and testis; moderately expressed in heart, muscle, adrenal gland, lymph nodes, thymus, and intestine; weakly expressed in spleen and kidney; and not detectable in liver, bone marrow, and stomach.

To examine the distribution of sema K1 mRNA in detail, in situ hybridization analysis was performed on tissue sections of embryonic day 11 and day 15 embryos, and on the brain and spinal cord sections of postnatal day 3 and 5 week old mice. A digoxigenin-labeled antisense RNA probe for sema K1 was used in this study. The sema K1 sense probe served as a control, which gave no significant hybridization signal on tissue sections of P3 and adult mice, but gave weak and uniform background signals in E11 and E15 tissue sections. Sema K1 mRNA does not appear to express significantly in the developing mouse embryo since no strong hybridization signals were detected in tissue sections generated from entire E11 and E15 embryos. Above background hybridization signal was detected in the ventral and lateral regions of the spinal cord at E11 and E15. At P3, the signal became more intense and expanded both dorsally and medially. By 5 weeks, strong hybridization signals were present in cells scattered throughout the gray matter except in the dorsal region where Rexed lamina layer I and II reside.

No significant expression of sema K1 mRNA is detected at E11 and E15 in the primodial cerebral cortex and cerebellum. At P3, intense expression of sema K1 mRNA become evident in the marginal zone of the cerebral neocortex. Moderate levels of expression were detected in the cortical plate and subplate. In the brain of 5 week old mice, the expression of sema K1 mRNA becomes widespread throughout the entire cerebral cortex. The level of mRNA expression is moderate among all lamina layers except layer I, where no expression is evident. In the cerebellum at P3, sema K1 message is strongly expressed in the external germinal layer and the primodial Purkinje cell layer. By 5 weeks, intense expression of sema K1 mRNA is found only in the Purkinje cells. In addition to the dynamic patterns of expression in spinal cord, cerebellum., and cortex, sema K1 mRNA is found to be present in other structures of adult brain, including the cochlear nucleus, inferior colliculus, hippocampus and dentate gyrus, the olfactory glomerular cell layer and mitral cell layer, and thalamic structures.

In vivo activity of sema K1 polypeptides. Rats (12 animals) receive a unilateral lesion of the nucleus basalis by infusion of ibotenic acid. Two weeks after the lesion, osmotic minipumps are implanted, that infuse 1 microgram human recombinant FLAGG-tagged dominant negative sema K1 polypeptide (SEQ ID NO:2, residues 180–634) per day into the lateral ventricle essentially as described in Andrews T J, et al. (1994) J Neurosci 14(5 Pt 2):3048–3058. A second group of rats (12 animals) is subjected to fluid-percussion brain injury alone followed by sema K1 infusion, essentially as described in Sinson G, et al. (1997) J Neurosurg 86(3):511–518. After two weeks of treatment, immunohistochemical analysis of cerebral sections reveal that exogenous sema K1 polypeptides enhance organotypic neurite outgrowth from damaged neurons undergoing nerve fiber atrophy.

In vivo activity of antisense sema K1 nucleic acids. Antisense oligonucleotides directed against sema K1 mRNA are administered intracerebroventricularly to twelve rats daily for two weeks substantially as described in Wan H Z, et al. (1998) J Nutr 128(2):287–291. Another twelve rats are administered intracerebroventricularly with missense oligonucleotides as controls. Immunohistochemical analysis of cerebral sections reveal significantly enhance neurite outgrowth and axon formation in the animals treated with the antisense oligonucleotides.

In vivo activity of anti-sema K1 antibodies. Anti-sema K1 antibodies are injected intraventricularly into eight rats and eight guinea pigs essentially as described in Costa M, et al. (1979) Brain Res 173(1):65–78. Immunohistochemical analysis of cerebral sections reveal that injection of anti-sema K1 antibodies inhibits degeneration of and enhances axon outgrowth from cerebral neurons in both rats and guinea-pigs. In rats it is necessary to infuse exogenous complement in the form of guinea-pie serum together with the anti-sema K 1, whereas in guinea-pigs the anti-sema K1 is effective on its own.

All publications and patent applications cited in this specification are herein incorporated by reference as if each individual publication or patent application were specifically and individually indicated to be incorporated by reference. Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

What is claimed is:

1. An isolated or recombinant polynucleotide encoding a polypeptide comprising a sequence selected from the group consisting of:
   (a) at least 100 contiguous residues of SEQ ID NO:2,
   (b) at least 60 contiguous residues of residues 340–634 of SEQ ID NO:2, and
   (c) at least 12 contiguous residues of residues 481–634 of SEQ ID NO:2,
   wherein the polypeptide has a functionality selected from the group consisting of enhancing organotypic neurite outgrowth from damaged neurons undergoing nerve fiber atrophy and eliciting a SemaK1-specific antibody.

2. A polynucleotide according to claim 1, said polypeptide comprising a sequence selected from the group consisting of: residues 1–10; residues 12–21; residues 25–37; residues 42–59; residues 62–71; residues 72–85; residues 88–89; residues 105–112; residues 116–122; residues 120–128; residues 175–182; residues 180–195; residues 201–208; residues 213–222; residues 222–230; residues 228–237; residues 230–338; residues 237–245; residues 247–256; residues 282–291; residues 335–353; residues 355–364; residues 365–374; residues 412–420; residues 440–447; residues 475–482; residues 480–495; residues 531–538; residues 554–562; residues 572–583; and residues 598–606 of SEQ ID NO:2.

3. A polynucleotide according to claim 1, said polypeptide comprising a sequence selected from the group consisting of: residues 8–606; residues 18–606; residues 26–606; residues 39–606; residues 48–606; residues 1–601; residues 1–592; residues 1–584; residues 1–573; residues 1–566; residues 24–587; residues 12–568; residues 41–601; residues 6–561; and residues 55–605 of SEQ ID NO:2.

4. A polynucleotide according to claim 1, said polypeptide comprising SEQ ID NO:2.

5. A polynucleotide according to claim 1, said polypeptide comprising at least 100 contiguous residues of SEQ ID NO:2.

6. A polynucleotide according to claim 1, said polypeptide comprising at least 60 contiguous residues of residues 340–634 of SEQ ID NO:2.

7. A polynucleotide according to claim 1, said polypeptide comprising at least 12 contiguous residues of residues 481–634 of SEQ ID NO:2.

8. An isolated or recombinant polynucleotide comprising SEQ ID NO:1, or a fragment thereof encoding a polypeptide comprising a sequence selected from the group consisting of:

(a) at least 100 contiguous residues of SEQ ID NO:2, (b) at least 60 contiguous residues of residues 340–634 of SEQ ID NO:2, and (c) at least 12 contiguous residues of residues 481–634 of SEQ ID NO:2, wherein the polypeptide has a functionality selected from the group consisting of enhancing organotypic neurite outgrowth from damaged neurons undergoing nerve fiber atrophy and eliciting a SemaK1-specific antibody.

9. A polynucleotide according to claim 8, said polypeptide comprising a sequence selected from the group consisting of: residues 1–10; residues 12–21; residues 25–37; residues 42–59; residues 62–71; residues 72–85; residues 88–89; residues 105–112; residues 116–122; residues 120–128; residues 175–182; residues 180–195; residues 201–208; residues 213–222; residues 222–230; residues 228–237; residues 230–338; residues 237–245; residues 247–256; residues 282–291; residues 335–353; residues 355–364; residues 365–374; residues 412–420; residues 440–447; residues 475–482; residues 480–495; residues 531–538; residues 554–562; residues 572–583; and residues 598–606 of SEQ ID NO:2.

10. A polynucleotide according to claim 8, said polypeptide comprising a sequence selected from the group consisting of: residues 8–606; residues 18–606; residues 26–606; residues 39–606; residues 48–606; residues 1–601; residues 1–592; residues 1–584; residues 1–573; residues 1–566; residues 24–587; residues 12–568; residues 41–601; residues 6–561; and residues 55–605 of SEQ ID NO:2.

11. A polynucleotide according to claim 8, said polypeptide comprising SEQ ID NO:2.

12. A polynucleotide according to claim 8, said polypeptide comprising at least 100 contiguous residues of SEQ ID NO:2.

13. A polynucleotide according to claim 8, said polypeptide comprising at least 60 contiguous residues of residues 340–634 of SEQ ID NO:2.

14. A polynucleotide according to claim 8, said polypeptide comprising at least 12 contiguous residues of residues 481–634 of SEQ ID NO:2.

15. A polynucleotide according to claim 8 comprising nucleotides 1–1902 of SEQ ID NO:1.

16. A polynucleotide according to claim 8 comprising SEQ ID NO:1.

* * * * *

UNITED STATES PATENT AND TRADEMARK OFFICE
CERTIFICATE OF CORRECTION

PATENT NO.    : 6,583,277 B2
DATED         : June 24, 2003
INVENTOR(S)   : Luo et al.

It is certified that error appears in the above-identified patent and that said Letters Patent is hereby corrected as shown below:

Column 29,
Line 5, after "SEQ ID NO:2", the period, "." should be a comma -- , --.

Signed and Sealed this

Twelfth Day of August, 2003

JAMES E. ROGAN
*Director of the United States Patent and Trademark Office*

SEQUENCE LISTING (1) GENERAL INFORMATION:

(iii) NUMBER OF SEQUENCES: 4

(2) INFORMATION FOR SEQ ID NO: 1:

(i) SEQUENCE CHARACTERISTICS:
      (A) LENGTH: 2498 base pairs
      (B) TYPE: nucleic acid
      (C) STRANDEDNESS: double
      (D) TOPOLOGY: linear (ii) MOLECULE TYPE: cDNA (ix) FEATURE:
      (A) NAME/KEY: CDS
      (B) LOCATION: 1..1902

(xi) SEQUENCE DESCRIPTION: SEQ ID NO: 1:

```
CTG CTG CTG CTG CTC TGG GCG GCC GCC GCC TCC GCC CAG GGC CAC CTA      48
Leu Leu Leu Leu Leu Trp Ala Ala Ala Ala Ser Ala Gln Gly His Leu
 1               5                  10                  15

AGG AGC GGA CCC CGC ATC TTC GCC GTC TGG AAA GGC CAT GTA GGG CAG      96
Arg Ser Gly Pro Arg Ile Phe Ala Val Trp Lys Gly His Val Gly Gln
             20                  25                  30

GAC CGG GTG GAC TTT GGC CAG ACT GAG CCG CAC ACG GTG CTT TTC CAC     144
Asp Arg Val Asp Phe Gly Gln Thr Glu Pro His Thr Val Leu Phe His
         35                  40                  45

GAG CCA GGC AGC TCC TCT GTG TGG GTG GGA GGA CGT GGC AAG GTC TAC     192
Glu Pro Gly Ser Ser Ser Val Trp Val Gly Gly Arg Gly Lys Val Tyr
     50                  55                  60

CTC TTT GAC TTC CCC GAG GGC AAG AAC GCA TCT GTG CGC ACG GTG AAT     240
Leu Phe Asp Phe Pro Glu Gly Lys Asn Ala Ser Val Arg Thr Val Asn
 65                  70                  75                  80

ATC GGC TCC ACA AAG GGG TCC TGT CTG GAT AAG CGG GAC TGC GAG AAC     288
Ile Gly Ser Thr Lys Gly Ser Cys Leu Asp Lys Arg Asp Cys Glu Asn
                 85                  90                  95

TAC ATC ACT CTC CTG GAG AGG CGG AGT GAG GGG CTG CTG GCC TGT GGC     336
Tyr Ile Thr Leu Leu Glu Arg Arg Ser Glu Gly Leu Leu Ala Cys Gly
            100                 105                 110

ACC AAC GCC CGG CAC CCC AGC TGC TGG AAC CTG GTG AAT GGC ACT GTG     384
Thr Asn Ala Arg His Pro Ser Cys Trp Asn Leu Val Asn Gly Thr Val
        115                 120                 125

GTG CCA CTT GGC GAG ATG AGA GGC TAC GCC CCC TTC AGC CCG GAC GAG     432
Val Pro Leu Gly Glu Met Arg Gly Tyr Ala Pro Phe Ser Pro Asp Glu
    130                 135                 140

AAC TCC CTG GTT CTG TTT GAA GGG GAC GAG GTG TAT TCC ACC ATC CGG     480
Asn Ser Leu Val Leu Phe Glu Gly Asp Glu Val Tyr Ser Thr Ile Arg
145                 150                 155                 160

AAG CAG GAA TAC AAT GGG AAG ATC CCT CGG TTC CGC CGC ATC CGG GGC     528
Lys Gln Glu Tyr Asn Gly Lys Ile Pro Arg Phe Arg Arg Ile Arg Gly
                165                 170                 175

GAG AGT GAG CTG TAC ACC AGT GAT ACT GTC ATG CAG AAC CCA CAG TTC     576
Glu Ser Glu Leu Tyr Thr Ser Asp Thr Val Met Gln Asn Pro Gln Phe
            180                 185                 190

ATC AAA GCC ACC ATC GTG CAC CAA GAC CAG GCT TAC GAT GAC AAG ATC     624
Ile Lys Ala Thr Ile Val His Gln Asp Gln Ala Tyr Asp Asp Lys Ile
        195                 200                 205

TAC TAC TTC TTC CGA GAG GAC AAT CCT GAC AAG AAT CCT GAG GCT CCT     672
Tyr Tyr Phe Phe Arg Glu Asp Asn Pro Asp Lys Asn Pro Glu Ala Pro
    210                 215                 220
```

-continued

```
CTC AAT GTG TCC CGT GTG GCC CAG TTG TGC AGG GGG GAC CAG GGT GGG          720
Leu Asn Val Ser Arg Val Ala Gln Leu Cys Arg Gly Asp Gln Gly Gly
225             230                 235                 240

GAA AGT TCA CTG TCA GTC TCC AAG TGG AAC ACT TTT CTG AAA GCC ATG          768
Glu Ser Ser Leu Ser Val Ser Lys Trp Asn Thr Phe Leu Lys Ala Met
            245                 250                 255

CTG GTA TGC AGT GAT GCT GCC ACC AAC AAG AAC TTC AAC AGG CTG CAA          816
Leu Val Cys Ser Asp Ala Ala Thr Asn Lys Asn Phe Asn Arg Leu Gln
            260                 265                 270

GAC GTC TTC CTG CTC CCT GAC CCC AGC GGC CAG TGG AGG GAC ACC AGG          864
Asp Val Phe Leu Leu Pro Asp Pro Ser Gly Gln Trp Arg Asp Thr Arg
            275                 280                 285

GTC TAT GGT GTT TTC TCC AAC CCC TGG AAC TAC TCA GCC GTC TGT GTG          912
Val Tyr Gly Val Phe Ser Asn Pro Trp Asn Tyr Ser Ala Val Cys Val
    290                 295                 300

TAT TCC CTC GGT GAC ATT GAC AAG GTC TTC CGT ACC TCC TCA CTC AAG          960
Tyr Ser Leu Gly Asp Ile Asp Lys Val Phe Arg Thr Ser Ser Leu Lys
305             310                 315                 320

GGC TAC CAC TCA AGC CTT CCC AAC CCG CGG CCT GGC AAG TGC CTC CCA         1008
Gly Tyr His Ser Ser Leu Pro Asn Pro Arg Pro Gly Lys Cys Leu Pro
            325                 330                 335

GAC CAG CAG CCG ATA CCC ACA GAG ACC TTC CAG GTG GCT GAC CGT CAC         1056
Asp Gln Gln Pro Ile Pro Thr Glu Thr Phe Gln Val Ala Asp Arg His
            340                 345                 350

CCA GAG GTG GCG CAG AGG GTG GAG CCC ATG GGG CCT CTG AAG ACG CCA         1104
Pro Glu Val Ala Gln Arg Val Glu Pro Met Gly Pro Leu Lys Thr Pro
            355                 360                 365

TTG TTC CAC TCT AAA TAC CAC TAC CAG AAA GTG GCC GTC CAC CGC ATG         1152
Leu Phe His Ser Lys Tyr His Tyr Gln Lys Val Ala Val His Arg Met
370             375                 380

CAA GCC AGC CAC GGG GAG ACC TTT CAT GTG CTT TAC CTA ACT ACA GAC         1200
Gln Ala Ser His Gly Glu Thr Phe His Val Leu Tyr Leu Thr Thr Asp
385             390                 395                 400

AGG GGC ACT ATC CAC AAG GTG GTG GAA CCG GGG GAG CAG GAG CAC AGC         1248
Arg Gly Thr Ile His Lys Val Val Glu Pro Gly Glu Gln Glu His Ser
            405                 410                 415

TTC GCC TTC AAC ATC ATG GAG ATC CAG CCC TTC CGC CGC GCG GCT GCC         1296
Phe Ala Phe Asn Ile Met Glu Ile Gln Pro Phe Arg Arg Ala Ala Ala
            420                 425                 430

ATC CAG ACC ATG TCG CTG GAT GCT GAG CGG AGG AAG CTG TAT GTG AGC         1344
Ile Gln Thr Met Ser Leu Asp Ala Glu Arg Arg Lys Leu Tyr Val Ser
            435                 440                 445

TCC CAG TGG GAG GTG AGC CAG GTG CCC CTG GAC CTG TGT GAG GTC TAT         1392
Ser Gln Trp Glu Val Ser Gln Val Pro Leu Asp Leu Cys Glu Val Tyr
450             455                 460

GGC GGG GGC TGC CAC GGT TGC CTC ATG TCC CGA GAC CCC TAC TGC GGC         1440
Gly Gly Gly Cys His Gly Cys Leu Met Ser Arg Asp Pro Tyr Cys Gly
465             470                 475                 480

TGG GAC CAA GGC CGC TGC ATC TCC ATC TAC AGC TCC GAA CGG TCA GTG         1488
Trp Asp Gln Gly Arg Cys Ile Ser Ile Tyr Ser Ser Glu Arg Ser Val
            485                 490                 495

CTG CAA TCC ATT AAT CCA GCC GAG CCA CAC AAG GAG TGT CCC AAC CCC         1536
Leu Gln Ser Ile Asn Pro Ala Glu Pro His Lys Glu Cys Pro Asn Pro
            500                 505                 510

AAA CCA GAC AAG GCC CCA CTG CAG AAG GTT TCC CTG GCC CCA AAC TCT         1584
Lys Pro Asp Lys Ala Pro Leu Gln Lys Val Ser Leu Ala Pro Asn Ser
            515                 520                 525

CGC TAC TAC CTG AGC TGC CCC ATG GAA TCC CGC CAC GCC ACC TAC TCA         1632
Arg Tyr Tyr Leu Ser Cys Pro Met Glu Ser Arg His Ala Thr Tyr Ser
530             535                 540
```

-continued

```
TGG CGC CAC AAG GAG AAC GTG GAG CAG AGC TGC GAA CCT GGT CAC CAG      1680
Trp Arg His Lys Glu Asn Val Glu Gln Ser Cys Glu Pro Gly His Gln
545                 550                 555                 560

AGC CCC AAC TGC ATC CTG TTC ATC GAG AAC CTC ACG GCG CAG CAG TAC      1728
Ser Pro Asn Cys Ile Leu Phe Ile Glu Asn Leu Thr Ala Gln Gln Tyr
                565                 570                 575

GGC CAC TAC TTC TGC GAG GCC CAG GAG GGC TCC TAC TTC CGC GAG GCT      1776
Gly His Tyr Phe Cys Glu Ala Gln Glu Gly Ser Tyr Phe Arg Glu Ala
            580                 585                 590

CAG CAC TGG CAG CTG CTG CCC GAG GAC GGC ATC ATG GCC GAG CAC CTG      1824
Gln His Trp Gln Leu Leu Pro Glu Asp Gly Ile Met Ala Glu His Leu
        595                 600                 605

CTG GGT CAT GCC TGT GCC CTG GCC GCC TCC CTC TGG CTG GGG GTG CTG      1872
Leu Gly His Ala Cys Ala Leu Ala Ala Ser Leu Trp Leu Gly Val Leu
    610                 615                 620

CCC ACA CTC ACT CTT GGC TTG CTG GTC CAC TAGGGCCTCC CGAGGCTGGG        1922
Pro Thr Leu Thr Leu Gly Leu Leu Val His
625                 630

CATGCCTCAG GCTTCTGCAG CCCAGGGCAC TAAAACGTCT CACACTCAGA GCCGGCTG      1982

CCGGGAGCTC CTTGCCTGCC ATTTTTTCCA GGGGACAGAA TAACCCAGTG GAGGATGC      2042

GGCCTGGAGA CGTCCAGCCG CAGGCGGCTG CTGGGCCCCA GGTGGCGCAC GGATGGTG      2102

GGGCTGAGAA TGAGGGCACC GACTGTGAAG CTGGGGCATC GATGACCCAA GACTTTAT      2162

TTTGGAAAAT ATTTTTCAGA CTCCTCAAAC TTGACTAAAT GCAGCGATGC TCCCAGCC      2222

AGAGCCCATG GGTCGGGGAG TGGGTTTGGA TAGGAGAGCT GGGATTCCAT CTCGACCC      2282

GGGCTGAGGC CTGAGTCCTT TTGGATTCTT GGTACCCACA TTGCCTCCTT CCCCTCCT      2342

TTTCAGGGGT GGGTGGTTGG TGTTCCTGAA GACCCAGGGA TACCCTTTGT CCAGCCCT      2402

CCTTGGCAGC TCCCTTTTTG GTCCTGGGTC CACAGGACA GCCGCCTTGC ATGTTTAT       2462

AAGGATGTTT GCTTTCCGGA CGGAAGGACG GAAAAA                              2498
```

(2) INFORMATION FOR SEQ ID NO: 2:

(i) SEQUENCE CHARACTERISTICS:
        (A) LENGTH: 634 amino acids
        (B) TYPE: amino acid
        (D) TOPOLOGY: linear (ii) MOLECULE TYPE: protein (xi) SEQUENCE DESCRIPTION: SEQ ID NO: 2:

```
Leu Leu Leu Leu Leu Trp Ala Ala Ala Ala Ser Ala Gln Gly His Leu
1               5                   10                  15

Arg Ser Gly Pro Arg Ile Phe Ala Val Trp Lys Gly His Val Gly Gln
            20                  25                  30

Asp Arg Val Asp Phe Gly Gln Thr Glu Pro His Thr Val Leu Phe His
        35                  40                  45

Glu Pro Gly Ser Ser Ser Val Trp Val Gly Gly Arg Gly Lys Val Tyr
    50                  55                  60

Leu Phe Asp Phe Pro Glu Gly Lys Asn Ala Ser Val Arg Thr Val Asn
65                  70                  75                  80

Ile Gly Ser Thr Lys Gly Ser Cys Leu Asp Lys Arg Asp Cys Glu Asn
                85                  90                  95

Tyr Ile Thr Leu Leu Glu Arg Arg Ser Glu Gly Leu Leu Ala Cys Gly
            100                 105                 110

Thr Asn Ala Arg His Pro Ser Cys Trp Asn Leu Val Asn Gly Thr Val
        115                 120                 125
```

```
Val Pro Leu Gly Glu Met Arg Gly Tyr Ala Pro Phe Ser Pro Asp Glu
    130                 135                 140

Asn Ser Leu Val Leu Phe Glu Gly Asp Glu Val Tyr Ser Thr Ile Arg
145                 150                 155                 160

Lys Gln Glu Tyr Asn Gly Lys Ile Pro Arg Phe Arg Ile Arg Gly
                165                 170                 175

Glu Ser Glu Leu Tyr Thr Ser Asp Thr Val Met Gln Asn Pro Gln Phe
            180                 185                 190

Ile Lys Ala Thr Ile Val His Gln Asp Gln Ala Tyr Asp Asp Lys Ile
        195                 200                 205

Tyr Tyr Phe Phe Arg Glu Asp Asn Pro Asp Lys Asn Pro Glu Ala Pro
    210                 215                 220

Leu Asn Val Ser Arg Val Ala Gln Leu Cys Arg Gly Asp Gln Gly Gly
225                 230                 235                 240

Glu Ser Ser Leu Ser Val Ser Lys Trp Asn Thr Phe Leu Lys Ala Met
                245                 250                 255

Leu Val Cys Ser Asp Ala Ala Thr Asn Lys Asn Phe Asn Arg Leu Gln
            260                 265                 270

Asp Val Phe Leu Leu Pro Asp Pro Ser Gly Gln Trp Arg Asp Thr Arg
        275                 280                 285

Val Tyr Gly Val Phe Ser Asn Pro Trp Asn Tyr Ser Ala Val Cys Val
    290                 295                 300

Tyr Ser Leu Gly Asp Ile Asp Lys Val Phe Arg Thr Ser Ser Leu Lys
305                 310                 315                 320

Gly Tyr His Ser Ser Leu Pro Asn Pro Arg Pro Gly Lys Cys Leu Pro
                325                 330                 335

Asp Gln Gln Pro Ile Pro Thr Glu Thr Phe Gln Val Ala Asp Arg His
            340                 345                 350

Pro Glu Val Ala Gln Arg Val Glu Pro Met Gly Pro Leu Lys Thr Pro
        355                 360                 365

Leu Phe His Ser Lys Tyr His Tyr Gln Lys Val Ala Val His Arg Met
    370                 375                 380

Gln Ala Ser His Gly Glu Thr Phe His Val Leu Tyr Leu Thr Thr Asp
385                 390                 395                 400

Arg Gly Thr Ile His Lys Val Val Glu Pro Gly Glu Gln Glu His Ser
                405                 410                 415

Phe Ala Phe Asn Ile Met Glu Ile Gln Pro Phe Arg Arg Ala Ala Ala
            420                 425                 430

Ile Gln Thr Met Ser Leu Asp Ala Glu Arg Arg Lys Leu Tyr Val Ser
        435                 440                 445

Ser Gln Trp Glu Val Ser Gln Val Pro Leu Asp Leu Cys Glu Val Tyr
    450                 455                 460

Gly Gly Gly Cys His Gly Cys Leu Met Ser Arg Asp Pro Tyr Cys Gly
465                 470                 475                 480

Trp Asp Gln Gly Arg Cys Ile Ser Ile Tyr Ser Ser Glu Arg Ser Val
                485                 490                 495

Leu Gln Ser Ile Asn Pro Ala Glu Pro His Lys Glu Cys Pro Asn Pro
            500                 505                 510

Lys Pro Asp Lys Ala Pro Leu Gln Lys Val Ser Leu Ala Pro Asn Ser
        515                 520                 525

Arg Tyr Tyr Leu Ser Cys Pro Met Glu Ser Arg His Ala Thr Tyr Ser
    530                 535                 540
```

```
Trp Arg His Lys Glu Asn Val Glu Gln Ser Cys Glu Pro Gly His Gln
545                 550                 555                 560

Ser Pro Asn Cys Ile Leu Phe Ile Glu Asn Leu Thr Ala Gln Gln Tyr
                565                 570                 575

Gly His Tyr Phe Cys Glu Ala Gln Glu Gly Ser Tyr Phe Arg Glu Ala
            580                 585                 590

Gln His Trp Gln Leu Leu Pro Glu Asp Gly Ile Met Ala Glu His Leu
        595                 600                 605

Leu Gly His Ala Cys Ala Leu Ala Ala Ser Leu Trp Leu Gly Val Leu
    610                 615                 620

Pro Thr Leu Thr Leu Gly Leu Leu Val His
625                 630

(2) INFORMATION FOR SEQ ID NO: 3:

(i) SEQUENCE CHARACTERISTICS:
        (A) LENGTH: 1818 base pairs
        (B) TYPE: nucleic acid
        (C) STRANDEDNESS: double
        (D) TOPOLOGY: linear (ii) MOLECULE TYPE: cDNA (ix) FEATURE:
        (A) NAME/KEY: CDS
        (B) LOCATION: 1..1818

(xi) SEQUENCE DESCRIPTION: SEQ ID NO: 3:

ATG GGC ACT TTG TGT GTT AGT ATT AGA TTA CTG ATG ATT TTA TCA GCC      48
Met Gly Thr Leu Cys Val Ser Ile Arg Leu Leu Met Ile Leu Ser Ala
635                 640                 645                 650

ATC ACA GCT GCT AAA TCT CGG TTT ATA GAT AAG CCA AGG CTG ATT GTT      96
Ile Thr Ala Ala Lys Ser Arg Phe Ile Asp Lys Pro Arg Leu Ile Val
                655                 660                 665

AAC CTA ACT GAT GGG TTT GGA CAG CAC CGG TTT TTT GGA CCC CAG GAA     144
Asn Leu Thr Asp Gly Phe Gly Gln His Arg Phe Phe Gly Pro Gln Glu
            670                 675                 680

CCA CAC ACT GTG CTT TTT CAC AGC CTC AAC TCT TCA GAC GTA TAT GTG     192
Pro His Thr Val Leu Phe His Ser Leu Asn Ser Ser Asp Val Tyr Val
        685                 690                 695

GGA GGT AAT AAT ACC ATC TAT TTG TTT GAT TTT GCT CAC AGC TCC AAC     240
Gly Gly Asn Asn Thr Ile Tyr Leu Phe Asp Phe Ala His Ser Ser Asn
    700                 705                 710

GCA TCC ACA GCT TTG ATA AAC ATA ACT AGC ACA CAT AAT ACC CAC CGG     288
Ala Ser Thr Ala Leu Ile Asn Ile Thr Ser Thr His Asn Thr His Arg
715                 720                 725                 730

TTA TCT AGT ACC TGC GAA AAC TTT ATA ACT CTG CTT CAT AAC CAG ACA     336
Leu Ser Ser Thr Cys Glu Asn Phe Ile Thr Leu Leu His Asn Gln Thr
                735                 740                 745

GAT GGG CTG CTA GCT TGT GGT ACT AAC TCA CAG AAA CCC AGC TGC TGG     384
Asp Gly Leu Leu Ala Cys Gly Thr Asn Ser Gln Lys Pro Ser Cys Trp
            750                 755                 760

CTG ATA AAC AAC CTA ACA ACT CAA TTT TTG GGG CCA AAA CTA GGC TTA     432
Leu Ile Asn Asn Leu Thr Thr Gln Phe Leu Gly Pro Lys Leu Gly Leu
        765                 770                 775

GCC CCC TTC TCA CCA TCA TCT GGC AAT CTG GTG CTG TTT GAC CAG AAT     480
Ala Pro Phe Ser Pro Ser Ser Gly Asn Leu Val Leu Phe Asp Gln Asn
    780                 785                 790

GAC ACC TAT TCC ACC ATT AAC CTC TAC AAG AGC CTC AGT GGC TCT CAC     528
Asp Thr Tyr Ser Thr Ile Asn Leu Tyr Lys Ser Leu Ser Gly Ser His
795                 800                 805                 810
```

```
                                          -continued

AAG TTT AGG AGG ATC GCT GGC CAA GTA GAA CTA TAC ACG AGT GAC ACC      576
Lys Phe Arg Arg Ile Ala Gly Gln Val Glu Leu Tyr Thr Ser Asp Thr
                815                 820                 825

GCC ATG CAC CGG CCA CAG TTT GTC CAG GCA ACA GCT GTG CAT AAA AAT      624
Ala Met His Arg Pro Gln Phe Val Gln Ala Thr Ala Val His Lys Asn
                830                 835                 840

GAA TCT TAT GAT GAT AAA ATC TAC TTT TTC TTT CAA GAA AAC AGC CAC      672
Glu Ser Tyr Asp Asp Lys Ile Tyr Phe Phe Phe Gln Glu Asn Ser His
                845                 850                 855

AGT GAC TTC AAA CAG TTT CCA CAT ACT GTA CCT AGA GTG GGG CAG GTG      720
Ser Asp Phe Lys Gln Phe Pro His Thr Val Pro Arg Val Gly Gln Val
                860                 865                 870

TGC TCT AGT GAT CAA GGT GGG GAG AGC TCC CTG TCT GTC TAC AAG TGG      768
Cys Ser Ser Asp Gln Gly Gly Glu Ser Ser Leu Ser Val Tyr Lys Trp
875                 880                 885                 890

ACC ACC TTT TTA AAA GCC AGA CTG GCG TGT GTA GAC TAT GAT ACT GGA      816
Thr Thr Phe Leu Lys Ala Arg Leu Ala Cys Val Asp Tyr Asp Thr Gly
                895                 900                 905

AGA ATC TAC AAT GAG CTA CAA GAT ATT TTC ATC TGG CAA GCC CCA GAG      864
Arg Ile Tyr Asn Glu Leu Gln Asp Ile Phe Ile Trp Gln Ala Pro Glu
                910                 915                 920

AAC AGC TGG GAA GAG ACT CTC ATC TAT GGA CTT TTT TTG AGC CCG TGG      912
Asn Ser Trp Glu Glu Thr Leu Ile Tyr Gly Leu Phe Leu Ser Pro Trp
                925                 930                 935

AAC TTT TCT GCG GTC TGT GTG TTT ACT GTA AAG GAC ATT GAC CAT GTG      960
Asn Phe Ser Ala Val Cys Val Phe Thr Val Lys Asp Ile Asp His Val
                940                 945                 950

TTT AAG ACA TCC AAG TTA AAA AAT TAT CAT CAT AAA CTC CCC ACA CCT     1008
Phe Lys Thr Ser Lys Leu Lys Asn Tyr His His Lys Leu Pro Thr Pro
955                 960                 965                 970

AGA CCA GGG CAA TGC ATG AAG AAC CAT CAG CAT GTT CCC ACA GAA ACC     1056
Arg Pro Gly Gln Cys Met Lys Asn His Gln His Val Pro Thr Glu Thr
                975                 980                 985

TTT CAG GTT GCT GAC AGA TAT CCA GAA GTT GCA GAT CCT GTA TAT CAG     1104
Phe Gln Val Ala Asp Arg Tyr Pro Glu Val Ala Asp Pro Val Tyr Gln
                990                 995                 1000

AAG AAC AAT GCC ATG TTT CCA ATA ATT CAG TCA AAA TAT ATC TAC ACC     1152
Lys Asn Asn Ala Met Phe Pro Ile Ile Gln Ser Lys Tyr Ile Tyr Thr
                1005                1010                1015

AAA CTA CTT GTT TAT AGG GTA GAG TAT GGA GGT GTT TTT TGG GCA ACT     1200
Lys Leu Leu Val Tyr Arg Val Glu Tyr Gly Gly Val Phe Trp Ala Thr
                1020                1025                1030

ATT TTT TAC CTC ACT ACC ATC AAA GGG ACT ATT CAT ATA TAT GTG AGG     1248
Ile Phe Tyr Leu Thr Thr Ile Lys Gly Thr Ile His Ile Tyr Val Arg
1035                1040                1045                1050

TAT GAA GAT TCC AAC TCT ACA ACA GCT CTC AAC ATT TTA GAG ATA AAT     1296
Tyr Glu Asp Ser Asn Ser Thr Thr Ala Leu Asn Ile Leu Glu Ile Asn
                1055                1060                1065

CCC TTT CAG AAG CCA GCC CCC ATA CAG AAT ATT CTT TTA GAT AAT ACA     1344
Pro Phe Gln Lys Pro Ala Pro Ile Gln Asn Ile Leu Leu Asp Asn Thr
                1070                1075                1080

AAT CTA AAG CTT TAT GTA AAT TCA GAG TGG GAG GTG AGT GAG GTG CCA     1392
Asn Leu Lys Leu Tyr Val Asn Ser Glu Trp Glu Val Ser Glu Val Pro
                1085                1090                1095

TTA GAC CTA TGT TCA GTG TAT GGG AAT GAT TGT TTC AGC TGT TTT ATG     1440
Leu Asp Leu Cys Ser Val Tyr Gly Asn Asp Cys Phe Ser Cys Phe Met
                1100                1105                1110

TCA AGG GAT CCC CTG TGC ACA TGG TAT AAC AAC ACC TGT TCC TTT AAA     1488
Ser Arg Asp Pro Leu Cys Thr Trp Tyr Asn Asn Thr Cys Ser Phe Lys
1115                1120                1125                1130
```

```
CAG AGA GTA TCT GTT GAA ACC GGT GGT CCA GCT AAC CGC ACC CTT TCA    1536
Gln Arg Val Ser Val Glu Thr Gly Gly Pro Ala Asn Arg Thr Leu Ser
            1135                1140                1145

GAA ATG TGT GGT GAC CAC TAT GCT CCA ACT GTG GTT AAG CAT CAA GTT    1584
Glu Met Cys Gly Asp His Tyr Ala Pro Thr Val Val Lys His Gln Val
            1150                1155                1160

TCT ATA CCT CTA TTA TCT AAT TCT TAT TTG TCC TGC CCA GCA GTC TCA    1632
Ser Ile Pro Leu Leu Ser Asn Ser Tyr Leu Ser Cys Pro Ala Val Ser
            1165                1170                1175

AAC CAC GCT GAC TAC TTT TGG ACT AAA GAT GGT TTC ACA GAA AAA AGA    1680
Asn His Ala Asp Tyr Phe Trp Thr Lys Asp Gly Phe Thr Glu Lys Arg
            1180                1185                1190

TGC CAT GTC AAA ACA CAC AAA AAT GAC TGC ATC TTG CTT ATA GCT AAC    1728
Cys His Val Lys Thr His Lys Asn Asp Cys Ile Leu Leu Ile Ala Asn
1195                1200                1205                1210

AGC ACG ACA GCC ACT AAT GGA ACC CAC GTG TGC AAC ATG AAA GAA GAT    1776
Ser Thr Thr Ala Thr Asn Gly Thr His Val Cys Asn Met Lys Glu Asp
            1215                1220                1225

TCG GTG ACA GTG AAA CTG TTA GAG GTG AAT GTG ACA CTG ATG            1818
Ser Val Thr Val Lys Leu Leu Glu Val Asn Val Thr Leu Met
            1230                1235                1240
```

(2) INFORMATION FOR SEQ ID NO: 4:

(i) SEQUENCE CHARACTERISTICS:
        (A) LENGTH: 606 amino acids
        (B) TYPE: amino acid
        (D) TOPOLOGY: linear (ii) MOLECULE TYPE: protein (xi) SEQUENCE DESCRIPTION: SEQ ID NO: 4:

```
Met Gly Thr Leu Cys Val Ser Ile Arg Leu Leu Met Ile Leu Ser Ala
 1               5                   10                  15

Ile Thr Ala Ala Lys Ser Arg Phe Ile Asp Lys Pro Arg Leu Ile Val
            20                  25                  30

Asn Leu Thr Asp Gly Phe Gly Gln His Arg Phe Phe Gly Pro Gln Glu
        35                  40                  45

Pro His Thr Val Leu Phe His Ser Leu Asn Ser Ser Asp Val Tyr Val
    50                  55                  60

Gly Gly Asn Asn Thr Ile Tyr Leu Phe Asp Phe Ala His Ser Ser Asn
65                  70                  75                  80

Ala Ser Thr Ala Leu Ile Asn Ile Thr Ser Thr His Asn Thr His Arg
            85                  90                  95

Leu Ser Ser Thr Cys Glu Asn Phe Ile Thr Leu Leu His Asn Gln Thr
            100                 105                 110

Asp Gly Leu Leu Ala Cys Gly Thr Asn Ser Gln Lys Pro Ser Cys Trp
            115                 120                 125

Leu Ile Asn Asn Leu Thr Thr Gln Phe Leu Gly Pro Lys Leu Gly Leu
    130                 135                 140

Ala Pro Phe Ser Pro Ser Ser Gly Asn Leu Val Leu Phe Asp Gln Asn
145                 150                 155                 160

Asp Thr Tyr Ser Thr Ile Asn Leu Tyr Lys Ser Leu Ser Gly Ser His
            165                 170                 175

Lys Phe Arg Arg Ile Ala Gly Gln Val Glu Leu Tyr Thr Ser Asp Thr
            180                 185                 190

Ala Met His Arg Pro Gln Phe Val Gln Ala Thr Ala Val His Lys Asn
            195                 200                 205
```

-continued

```
Glu Ser Tyr Asp Asp Lys Ile Tyr Phe Phe Gln Glu Asn Ser His
    210                 215                 220
Ser Asp Phe Lys Gln Phe Pro His Thr Val Pro Arg Val Gly Gln Val
225                 230                 235                 240
Cys Ser Ser Asp Gln Gly Gly Glu Ser Ser Leu Ser Val Tyr Lys Trp
                245                 250                 255
Thr Thr Phe Leu Lys Ala Arg Leu Ala Cys Val Asp Tyr Asp Thr Gly
            260                 265                 270
Arg Ile Tyr Asn Glu Leu Gln Asp Ile Phe Ile Trp Gln Ala Pro Glu
        275                 280                 285
Asn Ser Trp Glu Glu Thr Leu Ile Tyr Gly Leu Phe Leu Ser Pro Trp
    290                 295                 300
Asn Phe Ser Ala Val Cys Val Phe Thr Val Lys Asp Ile Asp His Val
305                 310                 315                 320
Phe Lys Thr Ser Lys Leu Lys Asn Tyr His His Lys Leu Pro Thr Pro
                325                 330                 335
Arg Pro Gly Gln Cys Met Lys Asn His Gln His Val Pro Thr Glu Thr
            340                 345                 350
Phe Gln Val Ala Asp Arg Tyr Pro Glu Val Ala Asp Pro Val Tyr Gln
        355                 360                 365
Lys Asn Asn Ala Met Phe Pro Ile Ile Gln Ser Lys Tyr Ile Tyr Thr
    370                 375                 380
Lys Leu Leu Val Tyr Arg Val Glu Tyr Gly Gly Val Phe Trp Ala Thr
385                 390                 395                 400
Ile Phe Tyr Leu Thr Thr Ile Lys Gly Thr Ile His Ile Tyr Val Arg
                405                 410                 415
Tyr Glu Asp Ser Asn Ser Thr Thr Ala Leu Asn Ile Leu Glu Ile Asn
            420                 425                 430
Pro Phe Gln Lys Pro Ala Pro Ile Gln Asn Ile Leu Leu Asp Asn Thr
        435                 440                 445
Asn Leu Lys Leu Tyr Val Asn Ser Glu Trp Glu Val Ser Glu Val Pro
    450                 455                 460
Leu Asp Leu Cys Ser Val Tyr Gly Asn Asp Cys Phe Ser Cys Phe Met
465                 470                 475                 480
Ser Arg Asp Pro Leu Cys Thr Trp Tyr Asn Asn Thr Cys Ser Phe Lys
                485                 490                 495
Gln Arg Val Ser Val Glu Thr Gly Gly Pro Ala Asn Arg Thr Leu Ser
            500                 505                 510
Glu Met Cys Gly Asp His Tyr Ala Pro Thr Val Val Lys His Gln Val
        515                 520                 525
Ser Ile Pro Leu Leu Ser Asn Ser Tyr Leu Ser Cys Pro Ala Val Ser
    530                 535                 540
Asn His Ala Asp Tyr Phe Trp Thr Lys Asp Gly Phe Thr Glu Lys Arg
545                 550                 555                 560
Cys His Val Lys Thr His Lys Asn Asp Cys Ile Leu Leu Ile Ala Asn
                565                 570                 575
Ser Thr Thr Ala Thr Asn Gly Thr His Val Cys Asn Met Lys Glu Asp
            580                 585                 590
Ser Val Thr Val Lys Leu Leu Glu Val Asn Val Thr Leu Met
    595                 600                 605
```